(12) United States Patent
Nord et al.

(10) Patent No.: US 10,146,393 B2
(45) Date of Patent: Dec. 4, 2018

(54) METHOD AND APPARATUS PERTAINING TO RADIATION TREATMENT PLAN OPTIMIZATION STATES

(75) Inventors: Janne Nord, Espoo (FI); Jarkko Peltola, Tuusula (FI); Lauri Halko, Helsinki (FI); Tao Sun, Helsinki (FI)

(73) Assignee: Varian Medical Systems International AG, Steinhausen (CH)

( * ) Notice: Subject to any disclaimer, the term of this patent is extended or adjusted under 35 U.S.C. 154(b) by 113 days.

(21) Appl. No.: 13/484,946

(22) Filed: May 31, 2012

(65) Prior Publication Data
US 2013/0326405 A1    Dec. 5, 2013

(51) Int. Cl.
*G06F 3/048*   (2013.01)
*A61N 5/10*    (2006.01)

(52) U.S. Cl.
CPC ............ *G06F 3/048* (2013.01); *A61N 5/103* (2013.01)

(58) Field of Classification Search
CPC ............................... A61N 5/103; G06F 3/048
USPC ........... 715/810; 378/65, 165, 95, 97; 600/1; 250/492.1, 492.3, 252.1, 395, 389
See application file for complete search history.

(56) References Cited

U.S. PATENT DOCUMENTS

| | | | |
|---|---|---|---|
| 2004/0122308 A1* | 6/2004 | Ding | 600/407 |
| 2005/0111621 A1* | 5/2005 | Riker | A61N 5/1031 378/65 |
| 2007/0078306 A1* | 4/2007 | Allison et al. | 600/300 |
| 2009/0070138 A1* | 3/2009 | Langheier | G06F 19/3431 705/2 |
| 2009/0319897 A1* | 12/2009 | Kotler et al. | 715/711 |
| 2010/0104068 A1* | 4/2010 | Kilby et al. | 378/65 |
| 2012/0323599 A1* | 12/2012 | Bal | A61N 5/1031 705/2 |
| 2013/0191146 A1* | 7/2013 | Park | G06F 19/321 705/2 |
| 2013/0305166 A1* | 11/2013 | Bastide et al. | 715/753 |

OTHER PUBLICATIONS

Trading Techs. Int'l, Inc. v. CQG, Inc., 675 F. App'x 1001, 2017 U.S. App. LEXIS 834, Appeal No. 2016-1616 (Fed. Cir. 2017) (non-precedential) (Year: 2017).*

* cited by examiner

Primary Examiner — Justin R. Blaufeld
(74) Attorney, Agent, or Firm — Fitch, Even, Tabin & Flannery LLP

(57) ABSTRACT

A control circuit stores a plurality of radiation treatment plan states as pertain to optimization of a given radiation treatment plan. The control circuit detects a user's selection of a particular one of the plurality of radiation treatment plan states and responsively displays dose distribution information as corresponds to that selected state. The control circuit can automatically store at least some of those states and/or can provide the user with an opportunity to selectively save a particular state. The control circuit can provide the user with an opportunity to modify optimization objectives such that at least two of the states correspond to different optimization objectives for the radiation treatment plan. The control circuit can also display a radiation treatment plan state selector to facilitate the user selecting the particular state. An individual selector for each state can provide a visual indication of merit as pertains to each such state.

4 Claims, 4 Drawing Sheets

METHOD AND APPARATUS PERTAINING TO RADIATION TREATMENT PLAN OPTIMIZATION STATES

TECHNICAL FIELD

This invention relates generally to radiation treatment plan optimization.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient. For example, many treatment plans provide for exposing the target volume to possibly varying dosages of radiation from a number of different directions. Arc therapy, for example, comprises one such approach.

Such treatment plans are often optimized prior to use. (As used herein, "optimization" will be understood to refer to improving a candidate treatment plan without necessarily ensuring that the optimized result is, in fact, the singular best solution.) Many optimization approaches use an automated incremental methodology where various optimization results are calculated and tested in turn using a variety of automatically-modified treatment plan optimization parameters.

Unfortunately, a purely automated approach may not suffice to meet the needs of all application settings and patient presentations. Instead, the judgment and eye of an experienced and thoughtful technician can sometimes lead to a best compromise between achieving an appropriate dosing of a given target volume while avoiding detrimental dosing of non-targeted volumes. Present automated approaches do not necessarily well accommodate such human intervention in an efficient, helpful, and/or intuitive manner.

BRIEF DESCRIPTION OF THE DRAWINGS

The above needs are at least partially met through provision of the method and apparatus pertaining to radiation treatment plan optimization states described in the following detailed description, particularly when studied in conjunction with the drawings, wherein.

Figure 1:
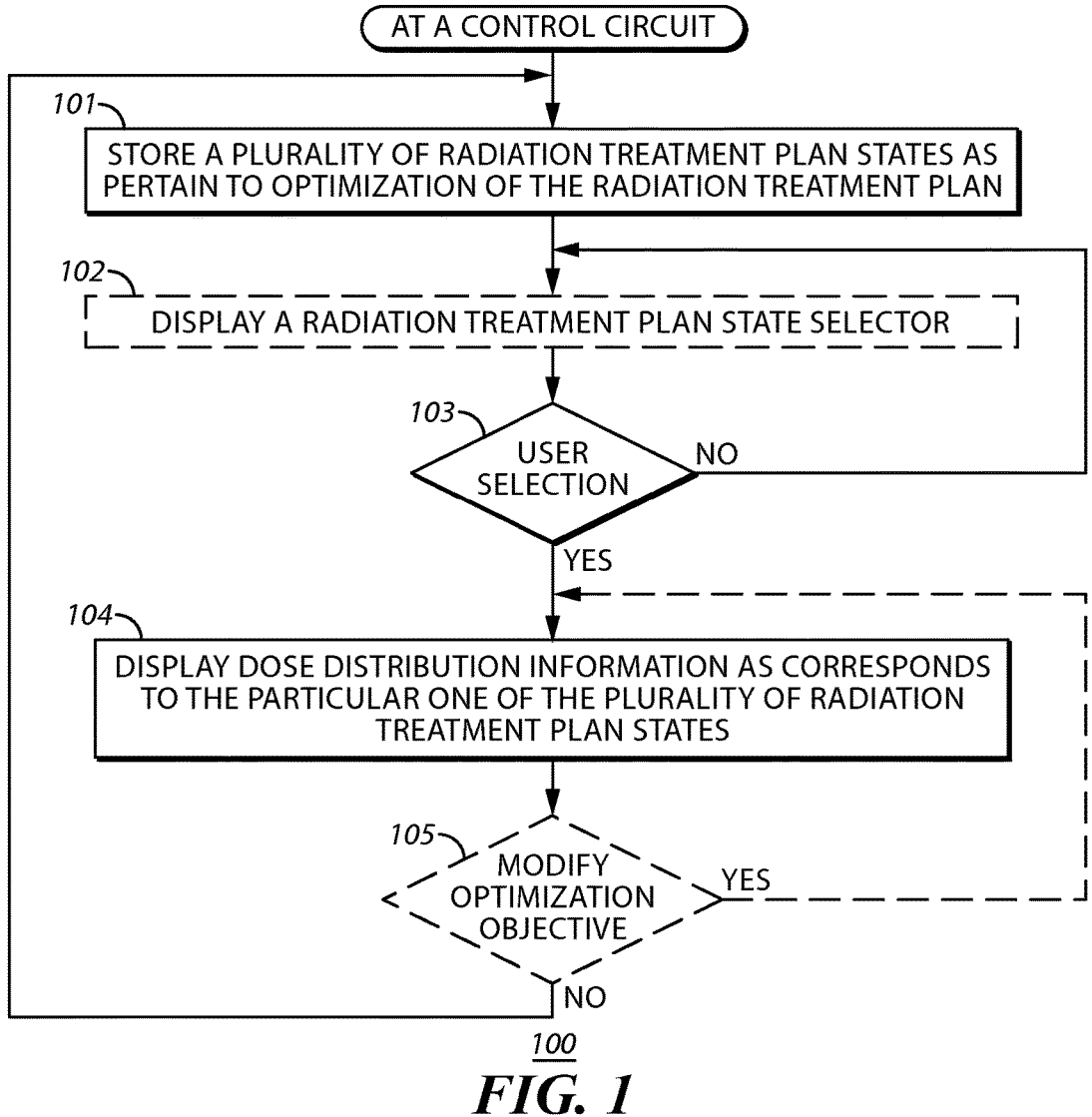
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments a control circuit stores a plurality of radiation treatment plan states as pertain to optimization of a given radiation treatment plan. The control circuit detects a user's selection of a particular one of the plurality of radiation treatment plan states and responsively displays dose distribution information as corresponds to that selected state.

These teachings will accommodate, if desired, automatically storing at least some of those radiation treatment plan states (for example, as a function of the passage of time or as a function of some particular event occurring). By another approach, and again as desired, these teachings will accommodate providing the user with an opportunity to selectively save a particular present radiation treatment plan state.

By one approach, the control circuit can also provide the user with an opportunity to modify one or more optimization objectives such that at least two of the plurality of radiation treatment plan states correspond to different optimization objectives for the radiation treatment plan.

If desired, these teachings will accommodate displaying a radiation treatment plan state selector to facilitate the user selecting the particular one of the plurality of radiation treatment plan states. This can comprise, for example, providing an individual selector for each of at least some of the radiation treatment plan states. By one approach, one or more of these radiation treatment plan state selectors can provide a visual indication of merit as pertains to each such state (such as, for example, a figure of merit as regards one or more optimization objectives as apply with respect to optimizing the radiation treatment plan).

So configured, a radiation treatment optimization process can proceed in an automated and incremental/iterative fashion to take advantage of the ordinary efficiencies associated with such methodology. At the same time, a user can readily and easily monitor and otherwise interact with the process in order to test and tweak particular approaches to identify potentially superior approaches that the automated process might never achieve or might require an undue amount of time to discover.

The present teachings are suitable for use with a wide variety of optimization approaches and can serve to greatly leverage the value and continued viability of such existing techniques. These teachings are also highly scalable and will accommodate essentially any number of radiation treatment plan states and/or optimization objectives. In many cases and application settings these teachings can be implemented and fielded in a highly economical manner as well.

These and other benefits may become clearer upon making a thorough review and study of the following detailed description. Referring now to the drawings, and in particular to FIG. 1, an illustrative process 100 that is compatible with many of these teachings will now be presented.

Figure 2:
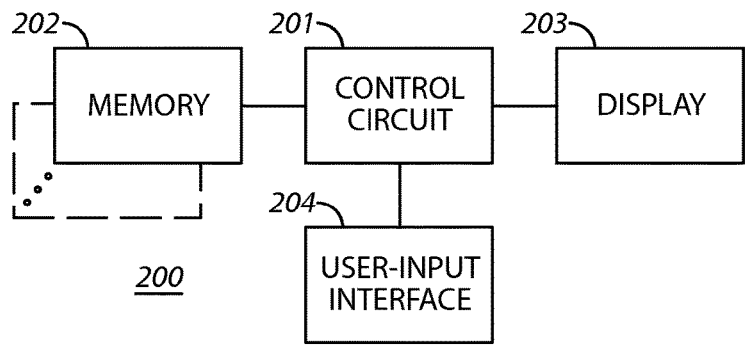
FIG. 2 comprises a block diagram as configured in accordance with various embodiments of the invention.

For the sake of illustration but without intending any particular limitations in these regards, this process 100 can be carried out by a control circuit of choice. With momentary reference to FIG. 2, a suitable processing apparatus 200 can include such a control circuit 201. Such a control circuit 201 can comprise a fixed-purpose hard-wired platform or can comprise a partially or wholly programmable platform. These architectural options are well known and understood in the art and require no further description here. This control circuit 201 is configured (for example, by using corresponding programming as will be well understood by those skilled in the art) to carry out one or more of the steps, actions, and/or functions described herein.

In this illustrative example the control circuit 201 operably couples to a memory 202. The memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201). It will also be understood that this "memory" can comprise a single discrete component or can comprise a plurality of such components that, in the aggregate, comprise this "memory."

This memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

In this illustrative example the control circuit 201 also operably couples to a display 203 and a user-input interface 204. This user-input interface 204 can comprise any of a variety of user-input mechanisms (such as, but not limited to, keyboards and keypads, cursor-control devices, touch-sensitive displays (in which case the user-input interface 204 and the display 203 can be integrally related to one another), speech-recognition interfaces, gesture-recognition interfaces, and so forth) to facilitate receiving information and/or instructions from a user.

Generally speaking, physical embodiments of such components are readily available and are often employed in combination with one another. Accordingly, for the sake of brevity further elaboration in these regards will not be provided here.

Referring again to FIG. 1, at step 101 this process 100 provides for storing a plurality of radiation treatment plan states as pertain to optimization of a corresponding radiation treatment plan. These radiation treatment plan states can be stored, for example, in the aforementioned memory 202.

To be clear, these radiation treatment plan states reflect the state of the radiation treatment plan at various times during the optimization process itself (including, if desired, various treatment-administration parameter values (and/or corresponding value ranges), optimization objectives, and/or the calculated results). When the optimization process comprises an automated process that works, in part, by automatically varying one or more treatment parameters (such as a particular configuration for a multi-leaf collimator, a particular energy level, a particular angle of exposure, and so forth) and then recalculating the resulting dose distribution with respect to a target volume (such as a tumor) in the patient and with respect to one or more non-targeted volumes (such as tissues in the vicinity of the target volume and/or specific critical organs), at least some of these radiation treatment plan states can each correspond to the dose distribution result(s) for a given set of presumed treatment parameters.

By one approach this step 101 can comprise automatically storing at least some of the plurality of radiation treatment plan states. By one simple approach this can comprise automatically storing the state information on some periodic sampling schedule. By another approach, used in combination with the foregoing or in lieu thereof, this step 101 can comprise storing any newly calculated state that exceeds some threshold measure of objective merit and that also varies from other previously-stored states in these same regards by at least some given variance. As yet another approach the automatic storing of such information can be triggered by specific predetermined events such as when the user makes changes to optimization objectives (as described below). The present teachings will accommodate other approaches in these regards as may be desired to meet the needs and/or to take advantage of whatever opportunities a given application setting may present.

The particular information stored as a "state" can vary as well with the application setting. Generally speaking, state information includes, directly or indirectly, the aforementioned dose distribution information along with the specific parameters that specify a given radiation treatment regimen, including the parameter settings for each field when the radiation treatment plan itself comprises a plurality of radiation-administration fields (as is the case, for example, with an arc therapy methodology).

The present teachings will also support, in combination with an automated storage approach or in lieu thereof, storing a given radiation treatment plan state as a response to a user having selected that particular radiation treatment plan state to be stored. With momentary reference to FIG. 3, when the aforementioned display 203 comprises a touch-sensitive display, at least a part of the aforementioned user-input interface 204 can include one or more selectable virtual buttons 301 that the control circuit 201 presents on the display 203. In such a case, one of these buttons 301 can comprise a STORE button 302 (either literally or at least functionally) that the user can assert (for example, by touching the display 203 at a location that coincides with the STORE button 302) to cause a present radiation treatment plan state to be stored as per step 101. By another approach, as when the display 203 does not comprise a touch-sensitive display, the user could manipulate, for example, a cursor control device such as a mouse to select and assert this STORE button 302.

At step 102 the process 100 shown in FIG. 1 presents an optional step of displaying a radiation treatment plan state selector to facilitate the user selecting a particular one of the aforementioned stored plurality of radiation treatment plan states. As illustrated by way of example in FIG. 3, this selector can comprise a portion 303 of the display 203 that presents an individual selector (some of which are denoted by reference numeral 304) for each of at least some of the radiation treatment plan states.

In this particular illustrative example each such individual selector 304 provides a visual indication of merit as pertains to each of the radiation treatment plan states. In particular, the relative height of each individual selector 304 provides this indication of merit. Accordingly, the individual selector denoted by reference numeral 305 represents a radiation treatment plan state having higher merit than, say, the individual selector denoted by reference numeral 306.

As will be disclosed below, these teachings will accommodate permitting the user to modify one or more optimization objectives during the course of the optimization process. Accordingly, it is possible that one radiation treatment plan state will reflect one value for a given optimization objective while another of the radiation treatment plan states will reflect another, different value for that optimization objective. In such a case, the aforementioned visual indication of merit can represent merit as regards different optimization objectives (including particular objectives as well as values/settings for given objectives) for the optimization of the radiation treatment plan. The presentation of the individual visual indications can then be normalized in some fashion, if desired, or left untouched in these regards.

Figure 3:
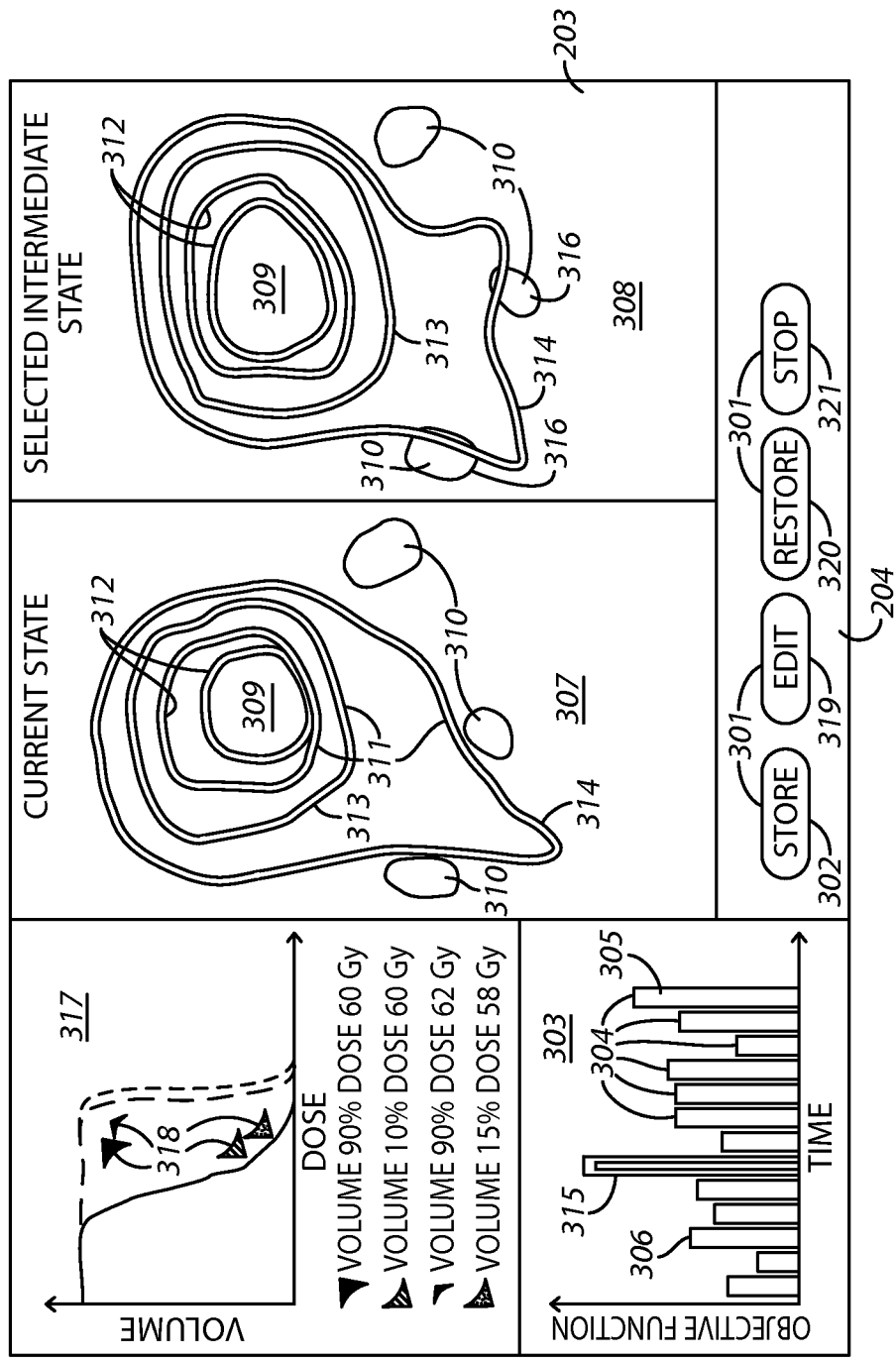
FIG. 3 comprises a screen shot as configured in accordance with various embodiments of the invention.

Referring still to both FIG. 1 and FIG. 3, upon detecting that a user has selected 103 a particular one of the plurality of radiation treatment plan states, at step 104 the process 100 provides for displaying dose distribution information as corresponds to the selected radiation treatment plan state. By one approach this can include co-presenting the dose distribution information for the selected state in combination with a display of dose distribution information as corresponds to a current radiation treatment plan state (i.e., a state that the optimization process has reached by completing, for example, a given number of processing iterations).

FIG. 3 illustrates that a first portion 307 of the display 203 can depict dose distribution information for the current state while a second portion 308 can present similar information for the selected state. In this example the two portions are similarly scaled and oriented in order to facilitate ease of visual comparison. Each of these views depicts a target volume 309 and three nearby non-targeted critical organs 310. These views also use isolines 311 to depict the areas of a particular level of dosing.

Colors (not shown) can serve to easily distinguish one isoline from another to help the viewer understand where considerable dosing occurs and where the dosing, though present, is less. By way of an illustrative example, the isolines denoted by reference numeral 312 in both views (which represent a relatively high level of dosing) can be colored red, the isolines denoted by reference numeral 313 in both views (which represent a moderate level of dosing) can be colored orange, and the isolines denoted by reference numeral 314 in both views (which represent a relatively low level of dosing) can be colored yellow.

In this illustrative example the current state as illustrated on the left-side portion 307 indicates that the current state avoids dosing any of the non-targeted areas of concern 310 (at least, with more than an amount of no present concern; some small dosing may in fact occur but not have a sufficient level to merit representation in these views).

The selected intermediate state as shown in right-side portion 308 corresponds to the particular radiation treatment plan state selector 315 that the user has selected in this particular example. To visually represent this selection, if desired and as shown, the selected radiation treatment plan state selector 315 can be highlighted in some manner. This can comprise using a different color, a representation of an illuminated, glowing state, flashing of all or part of the selector 315, or essentially any other approach to highlighting a display element that may be desired.

In this example, the selected intermediate state has the highest representation of merit. That said, and as illustrated in the dose distribution presentation that corresponds to the selected intermediate state, the lower levels of dosing as represented by the outer isoline 314 at least marginally intersects with two of the non-targeted volumes 316. In such a case the user can readily visually discern that the current state of the optimization process is slightly superior to the previously-best stored intermediate state. In this case, then, the user might choose to employ the previously-mentioned STORE button 302 to thereby store the current state to thereby render that state available for future use and/or comparison while then exploring other possible changes to the radiation treatment plan.

The process 100 of FIG. 1 can optionally support permitting the user to make non-automated changes to the operating specifications of the optimization process. By one approach, this can comprise providing the user with an opportunity 105 to modify at least one optimization objective.

Using this approach, it then becomes possible for two or more of the radiation treatment plan states to each correspond to different optimization objectives for the radiation treatment plan. Such an approach permits a user to make both subtle and non-subtle alterations with respect to the objectives of the radiation treatment plan being optimized and to have some ability to compare the corresponding results of utilizing those differing objectives to aid in deciding, for a particular patient and a particular application setting, a best objective (or objectives).

As shown in FIG. 3 another portion 317 of the display 203 can serve to present this opportunity to modify one or more optimization objectives 318. In this particular illustrative examples the optimization objectives 318 represent particular criteria regarding what percentage of the volume in question receives at least, or at most (as depends upon the nature of the objective) specified levels (in Grays) of radiation. Here, the user can select and move one of these optimization objectives 318 (for example, by clicking and dragging with mouse or by touching and swiping with a fingertip when using a touch-sensitive display) to thereby modify the optimization objective.

By one approach, if desired, an optional EDIT button 319 can serve to enable such changes. Using this approach, the user would first assert the EDIT button 319 and then make desired changes to the optimization objectives 318. These teachings will also accommodate, if desired, including a RESTORE button 320 to provide the user with an easy way to revert from a currently-modified set of optimization objectives 318 to a pre-modification state.

Eventually, the user may conclude that a particular state represents a suitable optimized result. By one approach a STOP button 321 provides a way for the user to signal that the optimization process is concluded.

These teachings are highly flexible in practice and will accommodate a considerable range of variations. Further examples in these regards will now be provided. It will be understood that these examples are provided for the sake of illustration and to demonstrate the breadth of these teachings and are offered with no intent of suggesting any limitations in these regards by way of their specificity.

FIRST EXAMPLE

Figure 4:
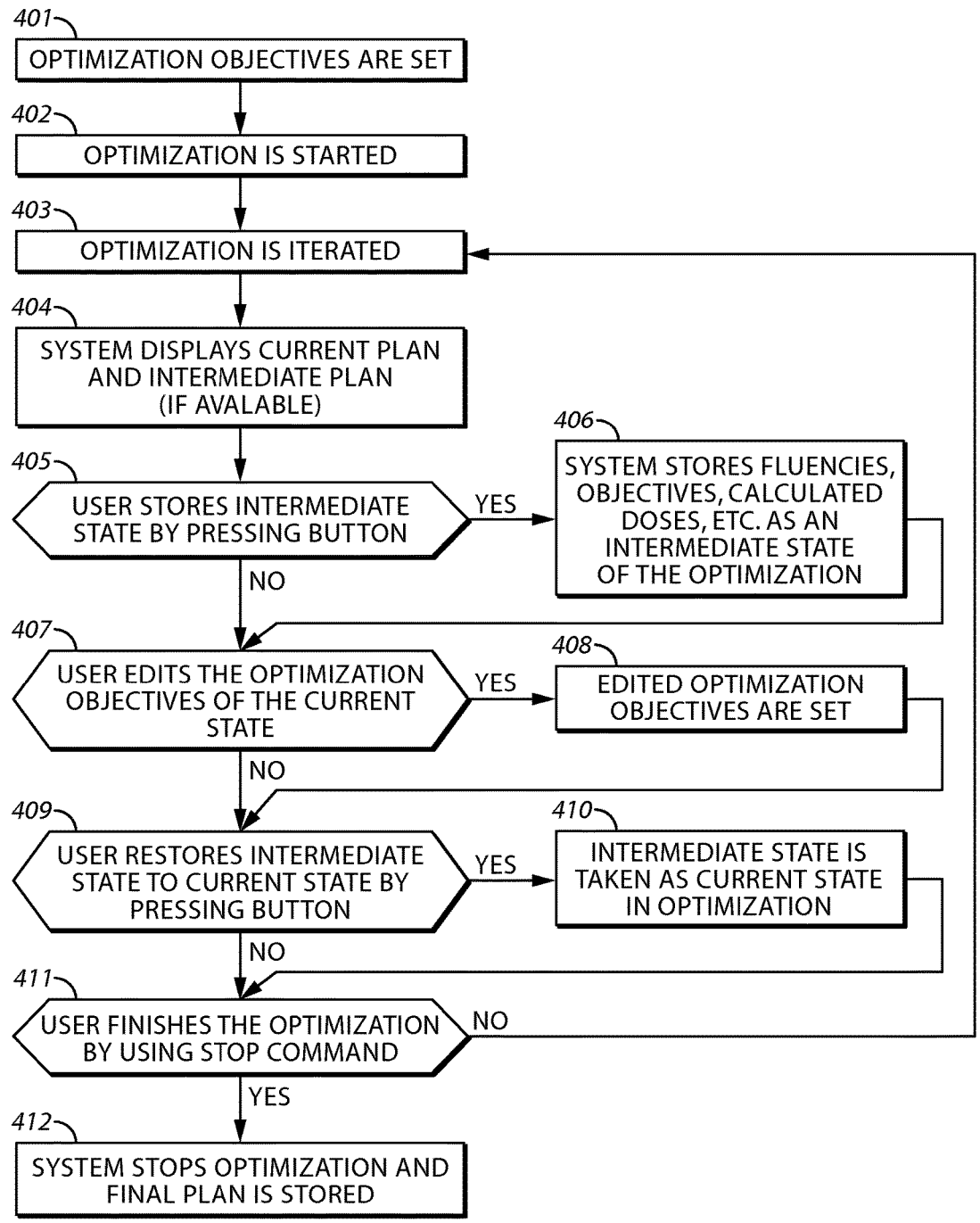
FIG. 4 comprises a flow diagram as configured in accordance with various embodiments of the invention.

The process 400 illustrated in FIG. 4 begins with setting 401 the optimization objectives. This can comprise an automatic activity and/or can be informed by specific choices entered by the user. The optimization process then starts 402 and the iterative process begins 403. As the iterative optimization process carries on, the system displays 404 the current plan state and at least one intermediate plan state (to the extent, of course, that an intermediate plan state yet exists; when the process first begins, such an intermediate plan state will typically not yet be available).

Upon detecting 405 that the user has pressed a store-function button the system stores information regarding the corresponding intermediate plan state. This can comprise, for example storing 407 fluencies, objectives, calculated doses, and so forth as the "state." (The reference to "fluencies" will be understood to refer to radiative flux integrated over time which comprises a fundamental metric in dosimetry (i.e., the measurement and calculation of an absorbed dose of ionizing radiation in matter and tissue).)

Upon detecting 407 that the user edits the optimization objectives as regards a current plan state, the process sets 408 the optimization objectives accordingly. If the system detects 409 that the user should then press a button that represents restore functionality, the process responds by taking 410 the intermediate state as the current state in terms of the optimization process.

The described process then continues the optimization iterations 403 and the foregoing series of activities unless and until the user uses 411 a stop command capability (such as a button that represents stop functionality), in which case the system stops 412 the optimization process and stores a corresponding final plan for treatment usage.

SECOND EXAMPLE

Figure 5:
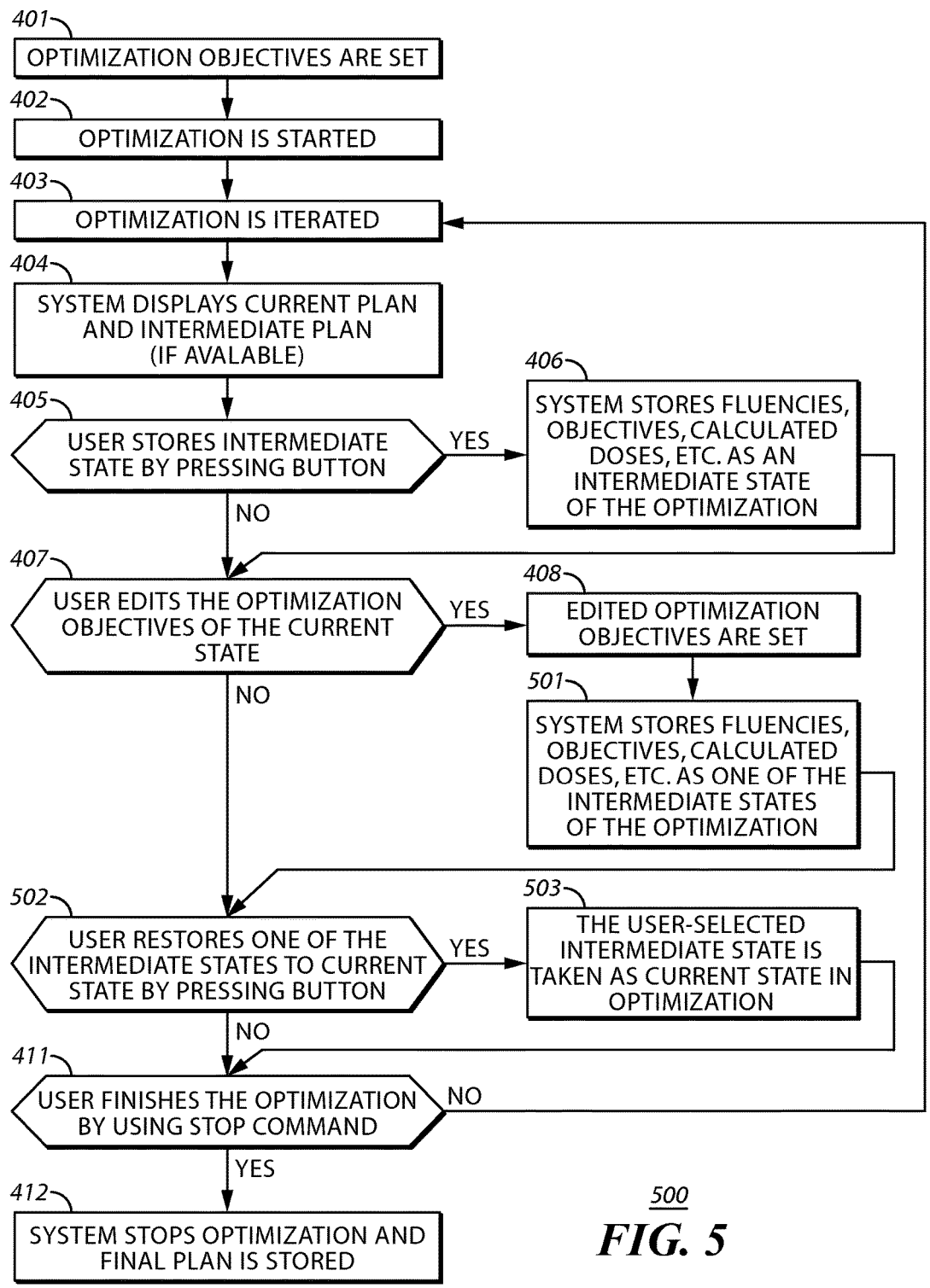
FIG. 5 comprises a flow diagram as configured in accordance with various embodiments of the invention.

The process 500 illustrated in FIG. 5 is very similar to the process 400 just described with respect to FIG. 4. In this second example, however, upon setting 408 edited optimization objectives as described above the process then automatically stores 501 the resultant fluencies, objectives, calculated doses, and so forth as one of the stored intermediate plan states.

The system now monitors to detect whether the user seeks to restore 502 one of the intermediate plan states to the current state and, upon detecting such an event, takes 503 the user-selected intermediate plan state as the current state.

These teachings provide a number of fundamental approaches that provide significant opportunities for a user to interact in meaningful yet efficient ways with an automated, iterative radiation treatment plan optimization engine. Such an approach, for many application settings, may better facilitate best use of both computation resources as well as the input and judgment of an expert technician.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

We claim:

1. A method performed by a control circuit, comprising:
executing an optimization process comprising:
determining a current output radiation treatment plan state by automatically varying at least one treatment parameter of the input radiation treatment plan;
determining whether to save information regarding the then-current output radiation treatment plan state as an intermediate state;
upon determining to save information regarding the then-current output radiation treatment plan state as an intermediate state, recalculating a resulting dose distribution with respect to a target volume in a patient and with respect to at least one non-targeted volume and automatically storing the information regarding the then-current output radiation treatment plan state as a corresponding intermediate state in a memory that is operably connected to the control circuit;
after executing the optimization process a first time, reiterating the optimization process one or more additional times, wherein, during each additional iteration, the automatically varying comprises one or more of: varying a different treatment parameter, or varying the same treatment parameters;
calculating, for each of the intermediate states, a corresponding merit value for a given optimization objective;
presenting, in a first portion of a display that is operably coupled to the control circuit, the resulting dose distribution information for the current output radiation treatment plan state of the optimization process;
presenting, in a second portion of the display, a plurality of individual selectors that each correspond to a different one of the stored intermediate states, wherein each of the individual selectors has a corresponding relative height that is based on the calculated merit value pertaining to the corresponding intermediate state;
detecting, via a user-input interface, a user's selection of a particular one of the plurality of individual selectors;
upon detecting a user's selection of a particular one of the plurality of individual selectors, displaying dose distribution information as corresponds to the intermediate state that corresponds to the selected particular one of the individual selectors in a third portion of the display, and highlighting the chosen selector;
detecting a user's modification of at least one optimization objective for the selected intermediate state; and
executing the optimization process using the user-modified radiation treatment plan state as the input radiation treatment plan.

2. The method of claim 1 wherein each of the individual selectors comprises, at least in part, a vertical bar.

3. An apparatus comprising:
a memory;
a display;
a user-input interface;
a control circuit operably coupled to the memory, the display, and the user-input interface and configured to:
execute an optimization process on an input radiation treatment plan, the optimization process comprising:
determining a current output radiation treatment plan state by automatically varying at least one treatment parameter of the input radiation treatment plan,
determining whether to save information regarding the then-current output radiation treatment plan state as an intermediate state;
upon determining to save information regarding then-current output radiation treatment plan state as an intermediate state, recalculating a resulting dose distribution with respect to a target volume in a patient and with respect to at least one non-targeted volume and automatically storing the information regarding the then-current output radiation treatment plan state as a corresponding intermediate state in the memory;

after executing the optimization process a first time, reiterate the optimization process one or more additional times, wherein, during each additional iteration, the automatically varying comprises one or more of: varying a different treatment parameter, or varying the same treatment parameters;

calculate, for each of the intermediate states, a corresponding merit value for a given optimization objective;

present, in a first portion of the display, the resulting dose distribution information for the current output radiation treatment plan state of the optimization process;

present, in a second portion of the display, a plurality of individual selectors that each correspond to a different one of the stored intermediate states, wherein each of the individual selectors has a corresponding relative height that is based on the calculated merit value pertaining to the corresponding intermediate state;

detect, via the user-input interface, a user's selection of a particular one of the plurality of individual selectors;

upon detecting the user's selection of the particular one of the individual selectors, display on the display dose distribution information as corresponds to the intermediate state that corresponds to the selected particular one of the individual selectors in a third portion of the display, and highlighting the chosen selector;

detect a user's modification of at least one optimization objective for the selected intermediate state; and execute the optimization process using the user-modified radiation treatment plan state as the input radiation treatment plan.

4. The apparatus of claim 3 wherein each of the individual selectors comprises, at least in part, a vertical bar.

* * * * *